(12) United States Patent
Chahine et al.

(10) Patent No.: US 11,896,394 B2
(45) Date of Patent: *Feb. 13, 2024

(54) ELECTRONICS-TO-TEXTILE INTERCONNECTION METHOD AND SYSTEM

(71) Applicant: MYANT INC., Toronto (CA)

(72) Inventors: Tony Chahine, Toronto (CA); Steve Aitken, Toronto (CA); Adrian Philip Straka, Toronto (CA); Milad Alizadeh-Meghrazi, Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/890,046

(22) Filed: Aug. 17, 2022

(65) Prior Publication Data

US 2022/0386958 A1  Dec. 8, 2022

Related U.S. Application Data

(63) Continuation of application No. 16/959,408, filed as application No. PCT/CA2018/051654 on Dec. 21, 2018, now Pat. No. 11,419,547.

(Continued)

(51) Int. Cl.
*A61B 5/00* (2006.01)
*H01R 12/70* (2011.01)
(Continued)

(52) U.S. Cl.
CPC ....... *A61B 5/6804* (2013.01); *H01R 12/7064* (2013.01); *H01R 12/7076* (2013.01);
(Continued)

(58) Field of Classification Search
CPC ... A61B 5/6804; A61B 5/25; A61B 2562/166; H01R 12/7064; H01R 12/7076; H01R 12/716; H05K 5/0026
(Continued)

(56) References Cited

U.S. PATENT DOCUMENTS 6,350,130 B1  2/2002  Eller et al.
8,758,241 B2  6/2014  Charles, Jr. et al.
(Continued)

FOREIGN PATENT DOCUMENTS

JP  1980136173  9/1980
JP  2009534546 A  9/2009
WO  2016054057 A1  4/2016

OTHER PUBLICATIONS

WIPO, International Search Report and Written Opinion of International Application No. PCT/CA2018/051654, dated Jun. 12, 2019.

(Continued)

*Primary Examiner* — Andargie M Aychillhum
(74) *Attorney, Agent, or Firm* — Norton Rose Fulbright Canada LLP

(57) ABSTRACT

An apparatus and method to reliably attach an electronic module to a textile. The overall mechanical assembly of the invention includes: (a) light pipe, (b) top enclosure, (b) magnet, (c) main electronics which contains (d) the main PCB, (e) battery and (f) other electronic components, (g) bottom enclosure, which holds (h) the connector PCB, (i) module dock, (j) top textile PCB which are located above the (j) textile band and under the (k) textile pocket and the (l) bottom textile PCB and (m) fabric and laminate padding, which are located below the textile band. The invention is physically embodied by an electronic module, comprising at least one printed circuit board (PCB), comprising at least one conductive circuit and at least one electronic component; a metallic rivet, grommet or eyelet to mechanically and electrically connect the; and a textile substrate with at least one electrically conductive circuit.

8 Claims, 14 Drawing Sheets

Related U.S. Application Data

(60) Provisional application No. 62/614,380, filed on Jan. 6, 2018.

(51) Int. Cl.
  *H01R 12/71*   (2011.01)
  *H05K 5/00*    (2006.01)
  *A61B 5/25*    (2021.01)
  *A61B 5/053*   (2021.01)
  *A61B 5/08*    (2006.01)

(52) U.S. Cl.
  CPC ......... *H01R 12/716* (2013.01); *H05K 5/0026* (2013.01); *A61B 5/053* (2013.01); *A61B 5/08* (2013.01); *A61B 5/25* (2021.01); *A61B 2560/0456* (2013.01); *A61B 2562/166* (2013.01); *H01R 2201/20* (2013.01)

(58) Field of Classification Search
  USPC .................................................. 361/749, 740
  See application file for complete search history.

(56) References Cited

U.S. PATENT DOCUMENTS

| | | |
|---|---|---|
| 9,028,404 B2 | 5/2015 | DeRemer et al. |
| 2002/0124295 A1 | 9/2002 | Fenwick et al. |
| 2007/0299325 A1 | 12/2007 | Farrell et al. |
| 2009/0035944 A1 | 2/2009 | Chaing et al. |
| 2012/0165645 A1 | 6/2012 | Russell et al. |
| 2018/0132748 A1* | 5/2018 | Perkins .................... A61B 5/08 |
| 2019/0027947 A1* | 1/2019 | Hopkins ............... H02J 7/0044 |

OTHER PUBLICATIONS

European Patent Office, Extended European Search Report dated Oct. 13, 2021 for European Patent Application No. 18898728.3.
Japanese Patent Office, Office Action dated Nov. 15, 2022 for Japanese Patent Application No. 2020-537183.
Japanese Patent Office, Office Action dated Apr. 18, 2023 for Japanese Patent Application No. 2020-537183.

\* cited by examiner

ELECTRONICS-TO-TEXTILE INTERCONNECTION METHOD AND SYSTEM

CROSS REFERENCE TO RELATED APPLICATIONS

This application is a continuation of U.S. patent application Ser. No. 16/959,408, filed on Jun. 30, 2020, and entitled "ELECTRONICS-TO-TEXTILE INTERCONNECTION METHOD AND SYSTEM", which is a U.S. National Stage Entry of PCT patent application number PCT/CA2018/051654, filed on Dec. 21, 2018, which claims priority from U.S. provisional patent application No. 62/614,380, filed on Jan. 6, 2018, the entire contents of which are hereby incorporated by reference herein.

TECHNICAL FIELD

The present invention relates in general to smart textiles. More specifically, the present invention relates to a method and system of connecting electronic components to electrically conductive textiles.

BACKGROUND

Smart textiles are a fabric based system of materials and structures that sense and react to environmental conditions or stimuli, such as those from mechanical, thermal, chemical, electrical, magnetic or other sources. Smart textiles can react or adapt to external stimuli or changing environmental conditions. The stimuli can include changes in temperature, moisture, pH, chemical sources, electric or magnetic fields, mechanical stress or strain.

Advanced smart textiles can have embedded computing, digital components, electronics, energy supply, and sensors. Basic components of smart textiles include sensors, actuators, data transmission and electrical power. When challenging functionality, size, cost, reliability, comfort and aesthetic/requirements are considered, there is an unmet need to seamlessly integrate electronic components into the manufacturing of the textiles. Further, electrical connections between electrically conductive circuits of the textiles (e.g. conductive fibres, wires, etc, of the textile substrate) with electronic components, such as power sources and computational components (e.g. processor, memory, etc.) require adaptable and/or reliable connection to the textiles.

Furthermore, textile manufacturing and electronics manufacturing use vastly different manufacturing infrastructures, utilizing highly dissimilar assembly equipment, materials and processes.

Hence, there is an urgent requirement for materials and manufacturing methods which can easily integrate the interconnection of electronics devices or electronics modules into textile based substrates.

SUMMARY

Provides is a method and system for docking to obviate or mitigate at least one of the above presented disadvantages.

A first aspect provided is a docking station assembly for providing a releasably secure connection between an electronic controller device and one or more conductive pathways of a textile substrate comprising: a module dock station having a body fixedly connected to a substrate assembly mounted on the textile substrate, the body exposing an electrical dock connector configured for mating with an electrical controller connector of the electronic controller device; the substrate assembly comprising: a first substrate positioned to one side of the textile substrate, such that one or more first electrical connection locations of the first substrate are aligned with the one or more conductive pathways, the first substrate having the electrical controller connector mounted thereon and electrically connected to the one or more first electrical connection locations by one or more respective substrate conductive pathways; a second substrate positioned on the other side of the textile substrate opposite the one side, the second substrate having one or more second electrical connection locations aligned with the one or more first electrical connection locations; and one or more respective fasteners fastening the one or more second electrical connection locations with the one or more first electrical connection locations, thus fixedly securing the textile substrate between the first substrate and the second substrate; wherein the one or more first electrical connection locations are in electrical contact with the adjacent one or more conductive pathways.

Provided is an apparatus and method to reliably attach an electronic module to a textile. The electronic module, comprises a printed circuit board (PCB), comprising at least one conductive circuit and at least one electronic component; a mechanically and electrically connection to the textile substrate; and the textile substrate with at least one electrically conductive circuit.

Optionally a rigid case to cover the PCB and electronic components on the PCB, and, optionally, a pocket to hold the rigid case, preferably knitted directly into the textile substrate. Finally, in a third optional embodiment, a magnet system to inhibit the module from moving within the pocket.

BRIEF DESCRIPTION OF THE DRAWINGS

The accompanying drawings, which are incorporated herein and form a part of the specification, illustrate the present invention and, together with the description, further explain the principles of the invention and to enable a person skilled in the pertinent art to make and use the invention.

DETAILED DESCRIPTION

In the following detailed description of the invention of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized and logical, mechanical, electrical, and other changes may be made without departing from the scope of the present invention. The following detailed description is, therefore, not to be taken in a limiting sense, and the scope of the present invention is defined only by the appended claims.

In the following description, specific details are set forth to provide a thorough understanding of the invention. However, it is understood that the invention may be practiced without these specific details. In other instances, well-known structures and techniques known to one of ordinary skill in the art have not been shown in detail in order not to obscure the invention. Referring to the figures, it is possible to see the various major elements constituting the apparatus of the present invention.

Figure 1:
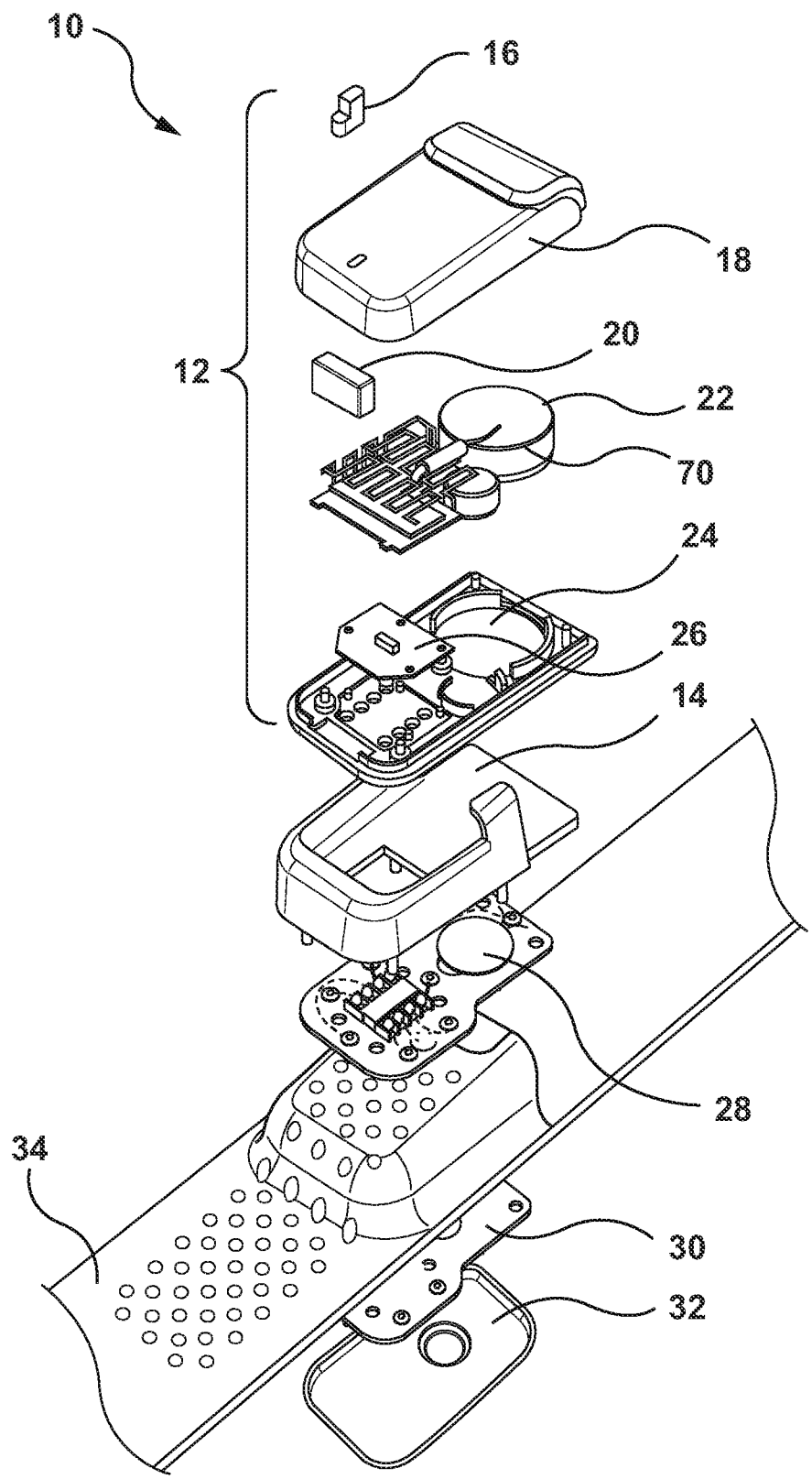
FIG. 1 illustrates an expanded (or exploded) view of the overall assembly.
Figure 4:
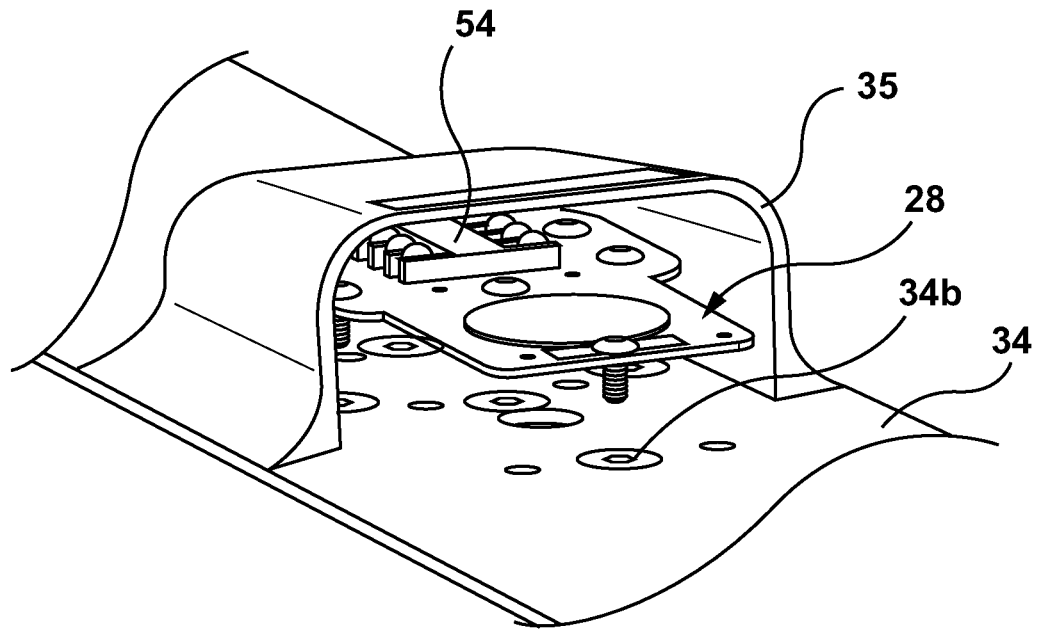
FIG. 4 illustrates a perspective view of the substrate component of FIG. 2 in relation to the textile substrate of FIG. 1.

Referring to FIG. 1, shown is an expanded (or exploded) view of an overall assembly 10 of a controller device 12 (e.g. electronic module) electrically connected to conductive pathways 80 (see FIG. 16) of a textile substrate 34 (e.g. in the form of a patch, band, shirt, pants, socks, undergarment, blanket, hat, glove, shoe, etc.) by way of a module dock station 14. As such, the module dock station 14 (see FIG. 5) can comprise a dock housing 50 having a body 14a with an aperture 52 for providing access between an electrical dock connector 54 (see FIG. 4) coupled to the conductive pathways 80 and an electrical controller connector 26 (see FIG. 1) that is connected to electronics 22 of the controller device 12, as further described below. The module dock station 14 can also have one or more clips 55 (as an example of a releasably securable mechanism for mechanically coupling with the housing 18,24 of the controller device 12). It is clear that the mating electrical connection between the electrical dock connector 54 and the electrical controller connector 26 is also releasably securable, thus facilitating repeated installation and removal of the controller device 12 with respect to the module dock station 14, both mechanically as well as electrically.

Periodic removal of the controller device 12 could be advantageous for recharging of a power source 70 (see FIG. 1) of the controller device 12, replacement/substitution of the controller device 12 (including the electronics 22), and/or temporary removal of the controller device 12 for washing/cleaning purposes of the textile substrate 34 (e.g. when washing a garment which integrally incorporates the textile substrate 34 as part of the overall garment construction).

Figure 6:
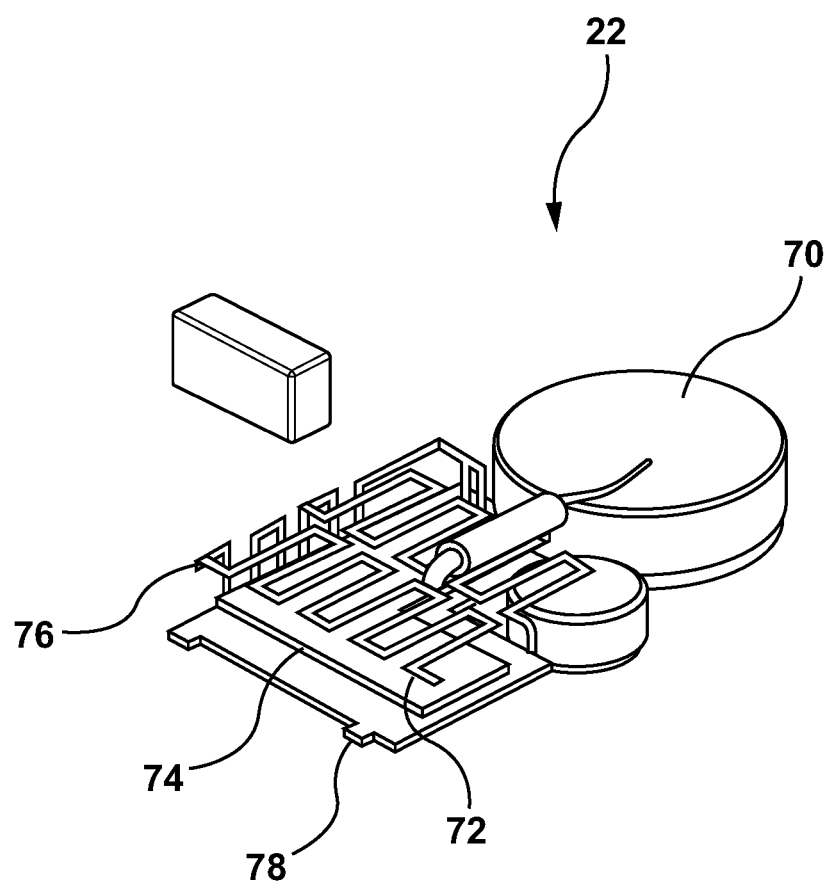
FIG. 6 provides an example of the electronic components of the controller device of FIG. 1.
Figure 7:
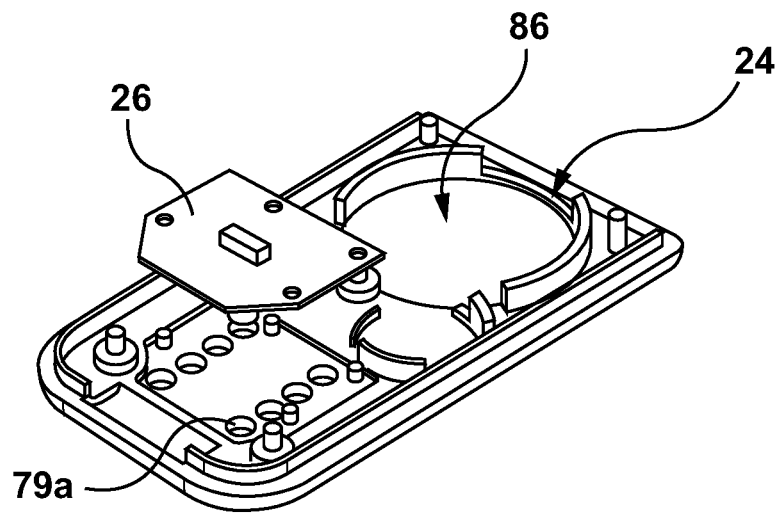
FIGS. 7 and 8 provide views of the interior of the controller device of FIG. 1.

Referring again to FIG. 1, the controller device 12 has a housing 18,24 (e.g. a top enclosure and a bottom enclosure) providing a moisture resistant housing for the enclosed electronics 22. For example, referring to FIG. 6, the electronics 22 can include a power source 70 (e.g. rechargeable battery) powering a memory 72 and a computer processor 74, such that the computer processor executes instructions store on the memory (e.g. ROM, RAM, etc.). The electrical connections between the electronics 22 can be by way of conductive pathways 76 (shown in concept) on a printed circuit board (PCB) or other electronics substrate 78. The conductive pathways 76 can be electrically connected to the electrical controller connector 26 (e.g. a socket connector—e.g. an 8 socket connector), such that the electrical controller connector 26 can be considered as integral within the housing 18,24 (see FIG. 7). As such, the electrical controller connector 26 can be considered as part of the controller device 12.

Figure 8:
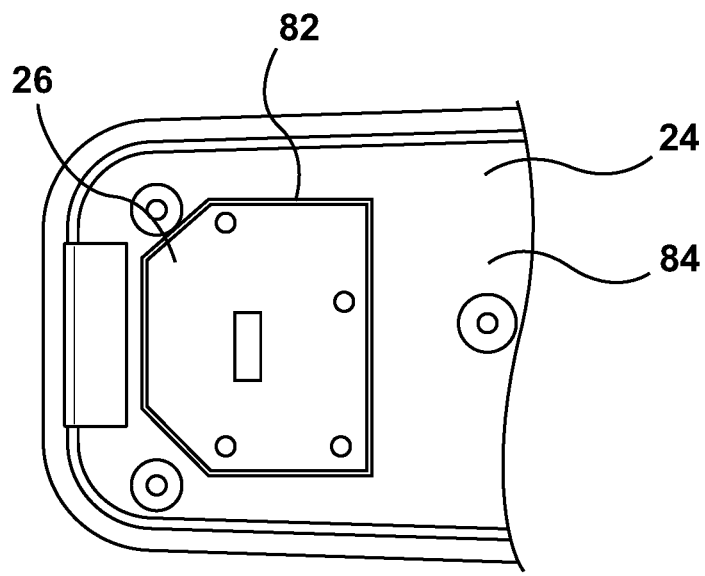

The bottom enclosure 24 of the housing can include apertures 79a for receiving corresponding pins 79b mounted on a body 54a of the electrical dock connector 54 (e.g. an 8 pin connector). It is also envisioned that the electrical dock connector 54 can be a socket connector and the electrical controller connector 26 can be a pin connector 26 configured for mating with the socket connector 54. It is also recognized that the electrical connectors 26,54 can have mating electrical connections other than of the pin/socket type (e.g. magnetic), as desired, in so much that the electrical connectors 26,54 are of the releasably securable type. As shown in FIG. 8, the electrical controller connector 26 can be sealed via a seal 82 (e.g. adhesive) with respect to an interior surface 84 (of the housing 18,24 when assembled). The seal 82 can be used to inhibit moisture or other foreign matter from entering into the interior 86 (see FIG. 7) via the apertures 79a (see FIG. 7).

Figure 2:
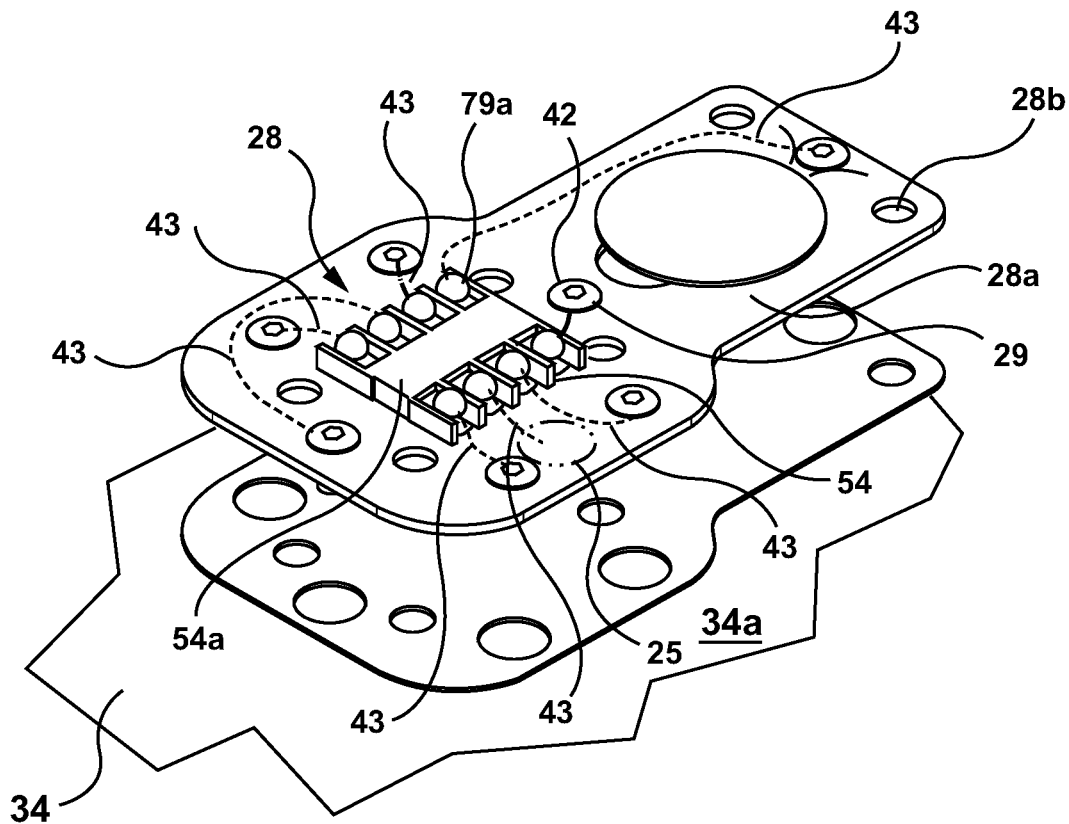
FIG. 2 illustrates a perspective view of a substrate component of the overall assembly of FIG. 1.

Referring again to FIG. 1, the overall assembly 10 also includes a first substrate 28 and a second substrate 30 for mounting on either side of the textile substrate 34. For example, the first substrate 28 can be a PCB. As shown in FIG. 2, the first substrate 28 has the electrical dock connector 54 mounted thereon, with conductive pathways 43 connecting each of the one or more electrical connectors 79b (e.g. pins, sockets, etc.) of the electrical dock connector 54 with corresponding one or more electrical connection locations 42 mounted on the first substrate 28. It is recognized that the one or more electrical connection locations 42 can be distributed about a surface 28a of the first substrate 28, such that each of the locations of the one or more electrical connection locations 42 correspond (e.g. in relative distance from one another) with the conductive pathways 80 (see FIG. 16) laid out on/in the textile substrate 34. The first substrate 28 can also have one or more electrical components 25 mounted thereon and thus electrically connected to the electronics 22 via the mated connectors 26,54 (pins/sockets) via corresponding conductive pathway(s) 43. As shown, the first substrate 28 can have a plurality of apertures 28b corresponding in spatial distribution with the spatial distribution of holes 34b of the textile substrate 34 (see FIG. 4). The apertures 28b are also matching in spatial distribution with a series of apertures 30b of a surface 30a of the second substrate 30 (e.g. a PCB). In assembly of the overall assembly 10, the first substrate 28 can be mounted on a corresponding surface 34a of the textile substrate 34 by an adhesive layer A. In assembly of the overall assembly 10, the second substrate 30 can be mounted on a corresponding opposing surface 34a of the textile substrate 34 by a similar adhesive layer A.

Figure 3:
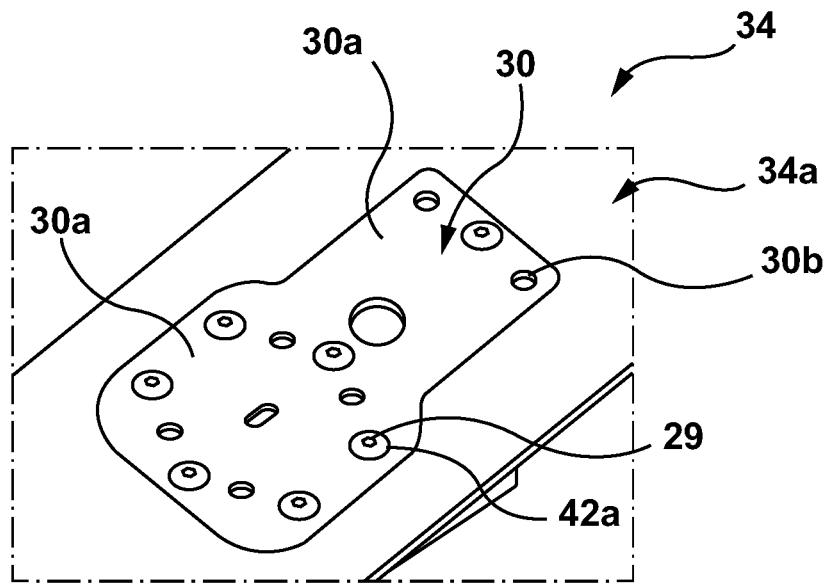
FIG. 3 illustrates a perspective view of a further substrate component of the overall assembly of FIG. 1.

Referring to FIG. 3, the second substrate 30 is mounted on an opposite surface 34a of the textile substrate 34 to that used to mount the first substrate 28, such that the textile substrate 34 is securely fastened between the substrates 28, 30, as further described below. The second substrate 30 also has connection locations 42a corresponding to the electrical connection locations 42, such that corresponding mechanical fasteners 29 (e.g. rivets—see FIG. 2) can be used to mechanically fasten the first substrate 28 to the second substrate 30, thus fixedly sandwiching/mounting the textile substrate 34 there-between).

Figure 5:
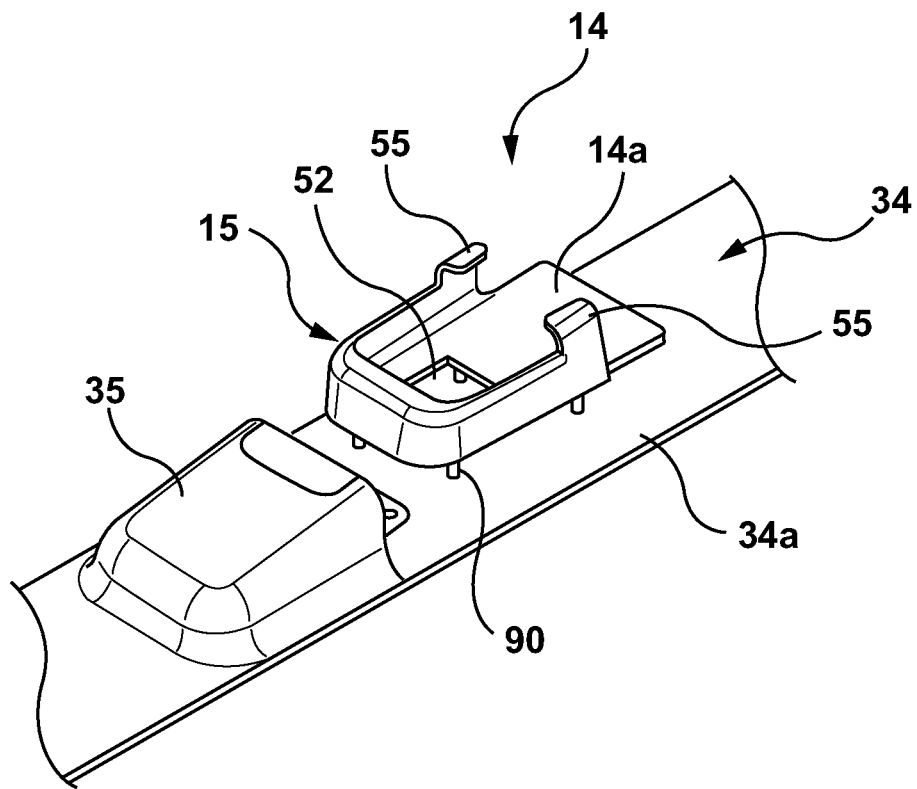
FIG. 5 illustrates a perspective view of a dock station body of FIG. 1 in relation to the textile substrate of FIG. 1.

Referring again to FIG. 4, an optional pocket 35 of the textile substrate 34 can be used to house the first substrate 28, as desired. As can be seen in FIG. 5, the optional pocket 35 can also be used to house the module dock station 14, when fastened to the first substrate 28 (further described below). Referring again to FIG. 1, the second substrate 30 can be covered by an optional backing 32 (e.g. fabric, plastic, padding, laminate, etc.) material, so as to provide for comfort of the wearer of the textile substrate 34 (e.g. as incorporated into a garment), when the backing 32 material is in contact with a skin of the wearer. The overall assembly 10 can also include a light pipe 16 (for indicating functional status of the electronics 22 via one or more visual indicators (e.g. LEDs) as well as a positioned magnet 20 in the interior 86 of the housing 18, 24. In summary, the housing 18, 24 of the controller device 12, once assembled, can be releasably secured, both mechanically and electrically, with the module dock station 14. The module dock station 14 is fixedly attached to the first substrate 28, which is in term fixedly attached to the textile substrate 34 via the mechanical (e.g. fasteners)/chemical (e.g. adhesive) connection between the first substrate 28 and the second substrate 30 when positioned on opposed sides 34a of the textile substrate 34.

Figure 9:
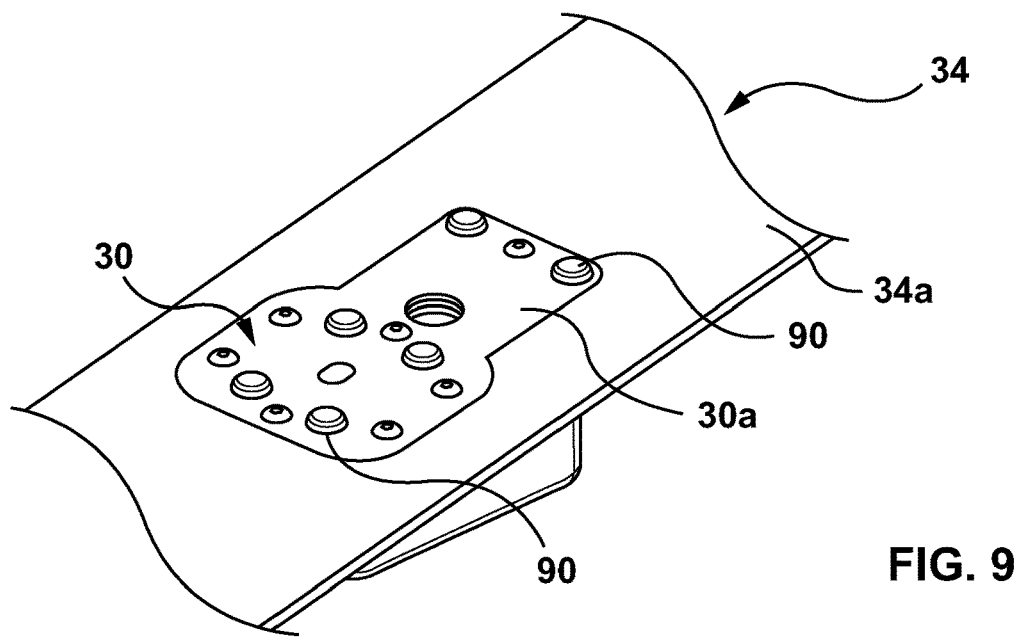
FIG. 9, 10, 11 provide views of the substrate component of FIG. 3 in relation to the textile substrate of FIG. 1.
Figure 15:
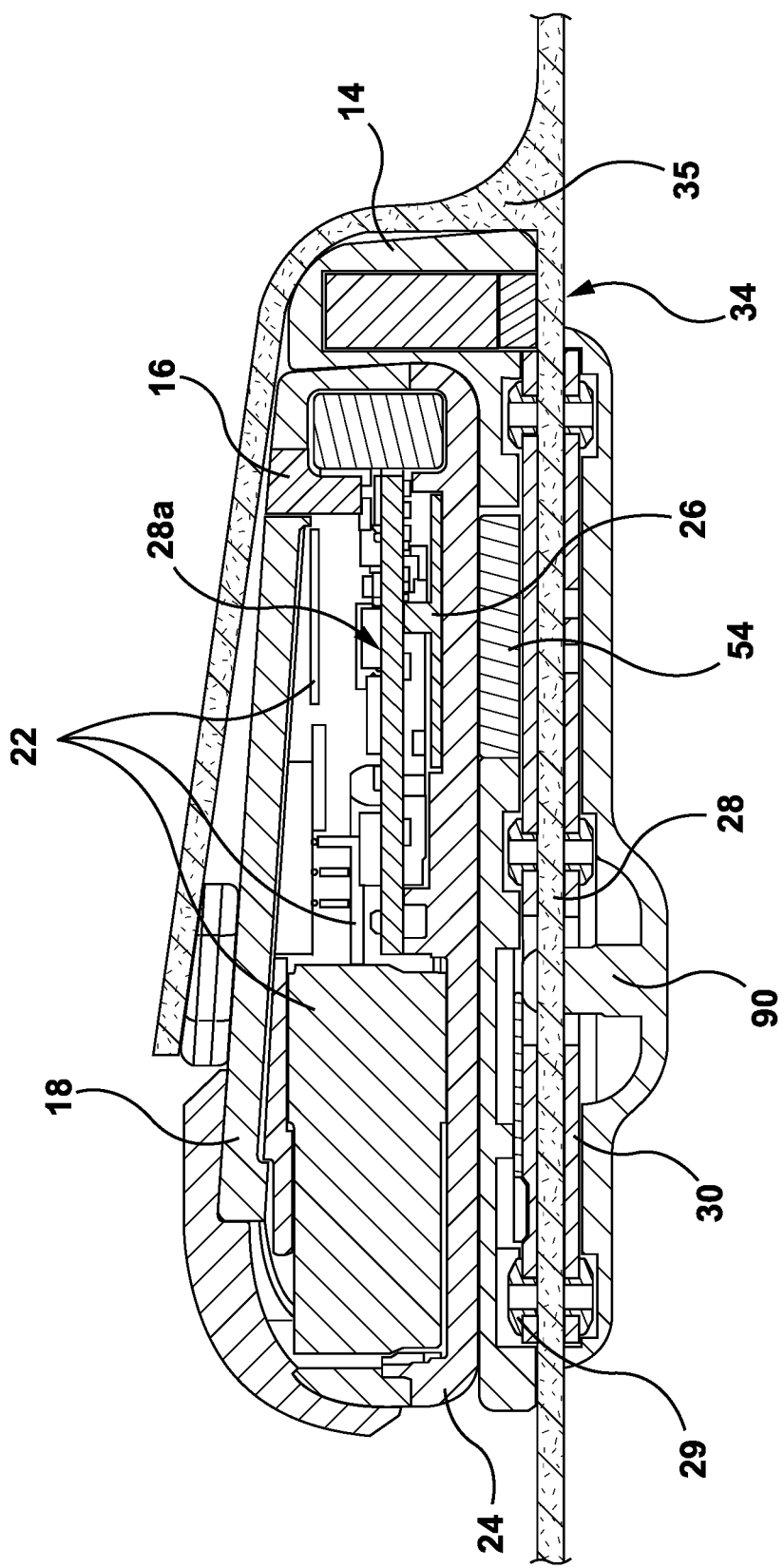
FIG. 15 illustrates a cross-sectional view of the entire overall assembly of FIG. 1 after assembly.

Referring again to FIGS. 2, 3, 4, the apertures 28b, 30b and holes 34b can be used to fasten the module docking station 14 with the substrate(s) 28, 30 to one another, thus fixedly securing the module docking station 14 to the textile substrate 34. For example, one fastening method of the module docking station 14 with the substrate(s) 28, 30 can be using a staking method (see FIGS. 5, 9, 15), whereby staking is the process of connecting the two components (the module docking station 14 with the substrate(s) 28, 30) by creating an interference fit of a fastener 90 between the two pieces (the module docking station 14 with the substrate(s) 28, 30). One workpiece 28, 30 has a hole 28b, 30b in it while the other (the module docking station 14) has a boss 90 that fits within the hole 28b, 30b. It is recognized that one of the workpieces 28, 30 can have the respective hole(s) 28b, 30b while the other of the pieces (the module docking station 14) can have the fastener(s) 90 mounted on the corresponding surface 28a, 30a. The fastener 90 (e.g. boss) can be very slightly undersized so that it forms a slip fit with the hole 28b, 30b. A staking punch can then be used to expand the boss 90 radially and to compress the boss 90 axially so as to form an interference fit between the workpieces (the module docking station 14 with the substrate(s) 28,30). This interference fit forms a permanent join(s)/connection(s) between the two pieces, such that the interposed textile substrate 34 is fixedly secured between the two substrates 28,30 which in turn is fastened to the module docking station 14 via the staking. The staking process can also be referred to as thermoplastic staking, also known as heat staking, which is the same process except that it uses heat to deform the plastic boss 90, instead of cold forming. A plastic stud 90 protruding from one component fits into a hole in the second component. The stud 90 is then deformed through the softening of the plastic to form a head which mechanically locks the two components (the module docking station 14 with the substrate(s) 28,30) together. Unlike welding techniques, staking has the capacity to join plastics to other materials (e.g. metal, PCB's) in addition to joining like or dissimilar plastics, and it has the advantage over other mechanical joining methods in reducing the need for consumables such as rivets and screws.

Figure 10:
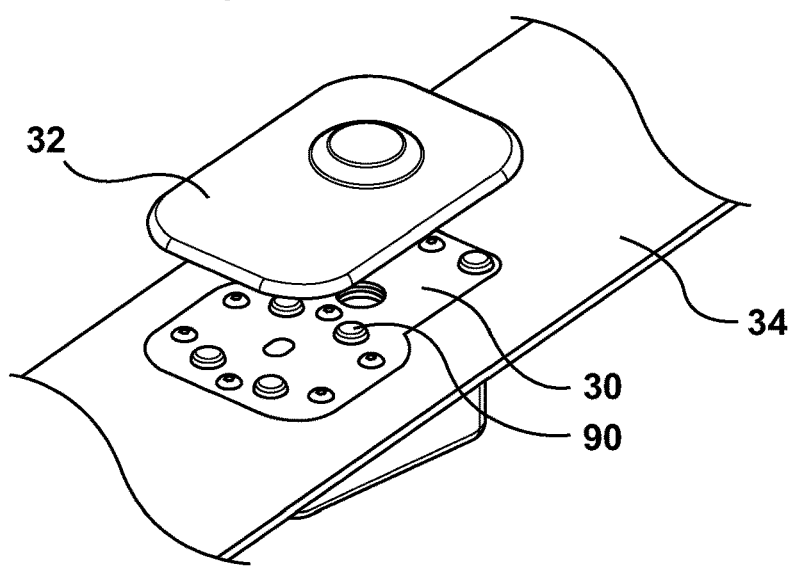
Figure 11:
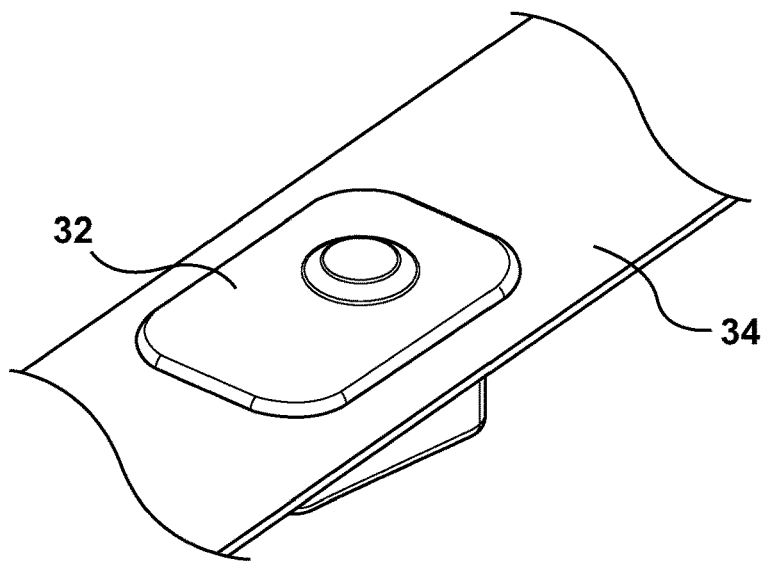
Figure 12:
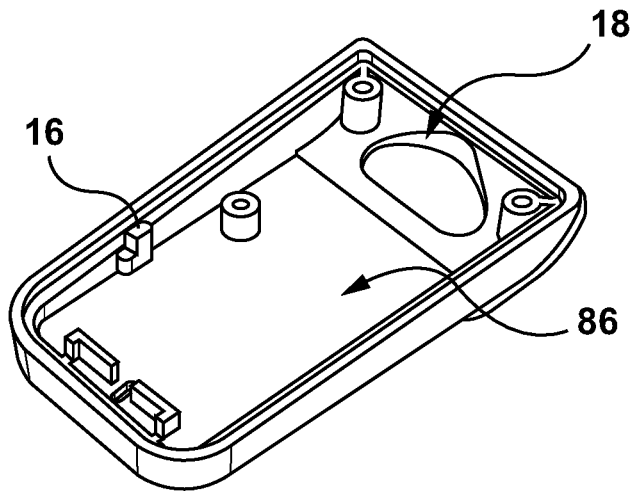
FIG. 12, 13, 14 provide views of the controller device of FIG. 1 in both assembled and unassembled.
Figure 13:
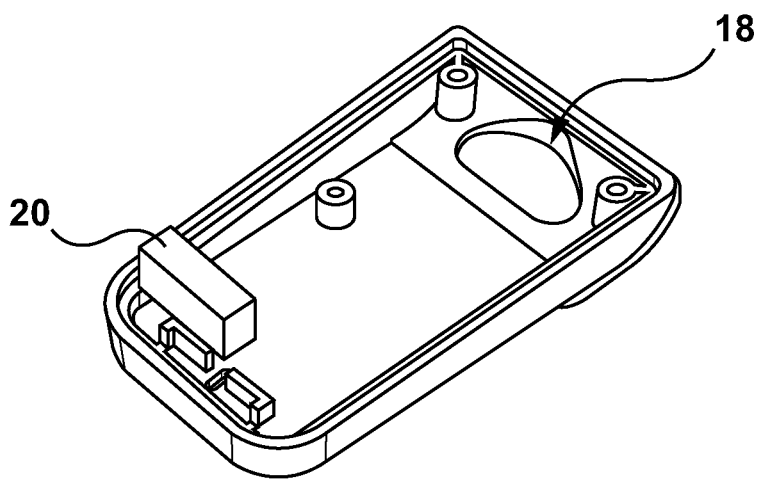
Figure 14:
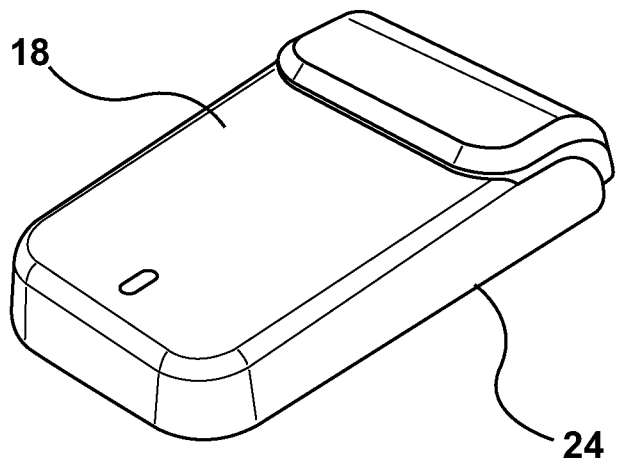
Figure 16:
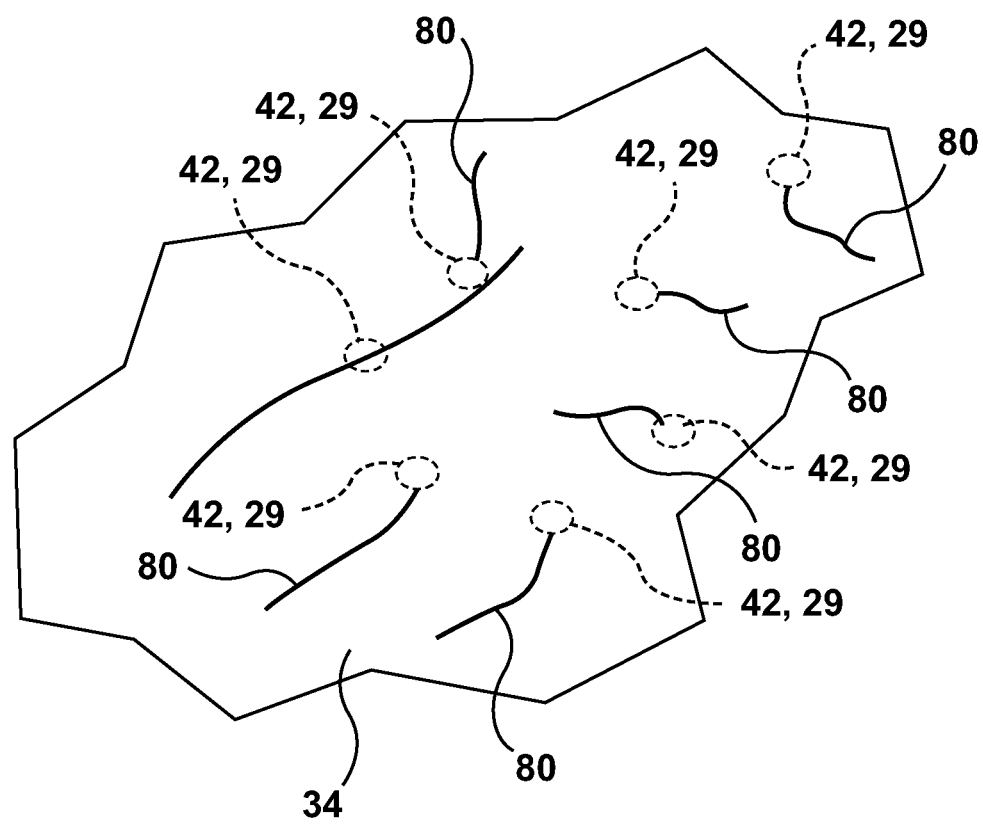
FIG. 16 is an example view of the textile substrate of FIG. 1 including conductive pathways.

Referring to FIGS. 10 and 11, shown is an example backing 32 in order to cover the second substrate 30 after being fastened to the first substrate 28. Referring to FIGS. 12, 13, 14, shown is the housing 18,24 in an unassembled and assembled form, such that the interior 86 with mounted light pipe 16 and magnet 20 are shown by example. Referring to FIG. 16, shown is a cross sectional view of the overall assembly 10, including an optional piezo sensor mounted between the first substrate 28 and the body 14a of the module dock station 14.

Referring to FIG. 16, shown is an example textile substrate 34 with the conductive pathways 80, as an illustration only, with the locations of the electrical connector locations 42 (and/or fasteners 29) of FIG. 2 in ghosted view. It is recognized that an electrical connection between the electrical connector locations 42 and the conductive pathways 80 is fixed when the electrical connector locations 42 (of the first substrate 28) come into contact with the conductive pathways 80, which is maintained due to 1) the fixed connection (e.g. via fasteners 90) between the substrates 28, 30 thus sandwiching the textile substrate 34 there between and biasing the electrical connectors locations 42 and the conductive pathways 80 into physical contact with one another; and/or 2) the connection via the fasteners 29 (e.g. conductive fasteners such as metal rivets, pins, etc.) between the substrates 28, 30 as the fasteners 29 are in physical contact with the electrical pathways 80 as well as the electrical connector locations 42. The substrates 28, 30 can be made of flexible or rigid material, as desired, so long as the material retains the interconnection between the locations 42 by the fasteners 29.

For example, electrical current to the electronics 22 follows the electrically conductive path of: a) from the conductive pathways 76 to b) the electrical controller connector 26 to c) the electrical dock connector 54 to d) the conductive pathways 43 connecting each of the one or more electrical connectors 79b (e.g. pins, sockets, etc.) of the electrical dock connector 54 to e) corresponding one or more electrical connection locations 42 to finally f) (e.g. via the fasteners 29) positioned adjacent to and electrically bonded to the conductive pathways 80 of the textile substrate 34. Similarly, electrical current from the conductive pathways 80 of the textile substrate 34 follows the electrically conductive path of: a) (e.g. via the fasteners 29) positioned adjacent to and electrically bonded to the conductive pathways 80 of the textile substrate 34 to b) corresponding one or more electrical connection locations 42 to c) the conductive pathways 43 connecting each of the one or more electrical connectors 79b (e.g. pins, sockets, etc.) of the electrical dock connector 54 to d) the electrical dock connector 54 to e) the electrical controller connector 26 to f) the conductive pathways 76 connected to the electronics 22.

Figure 17:
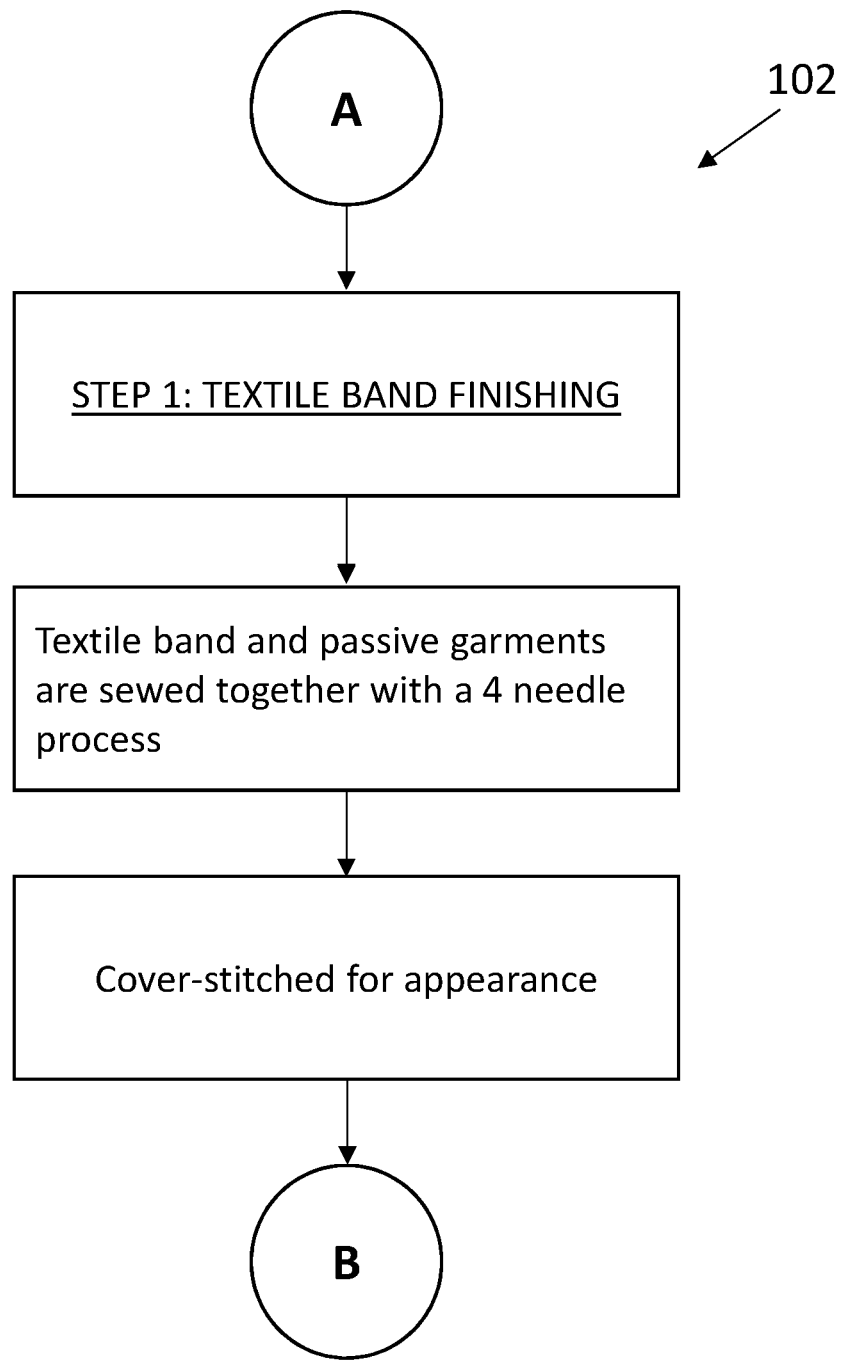
FIGS. 17-21 are example flowcharts of assembly methods for the overall assembly of FIG. 1.
Figure 18:
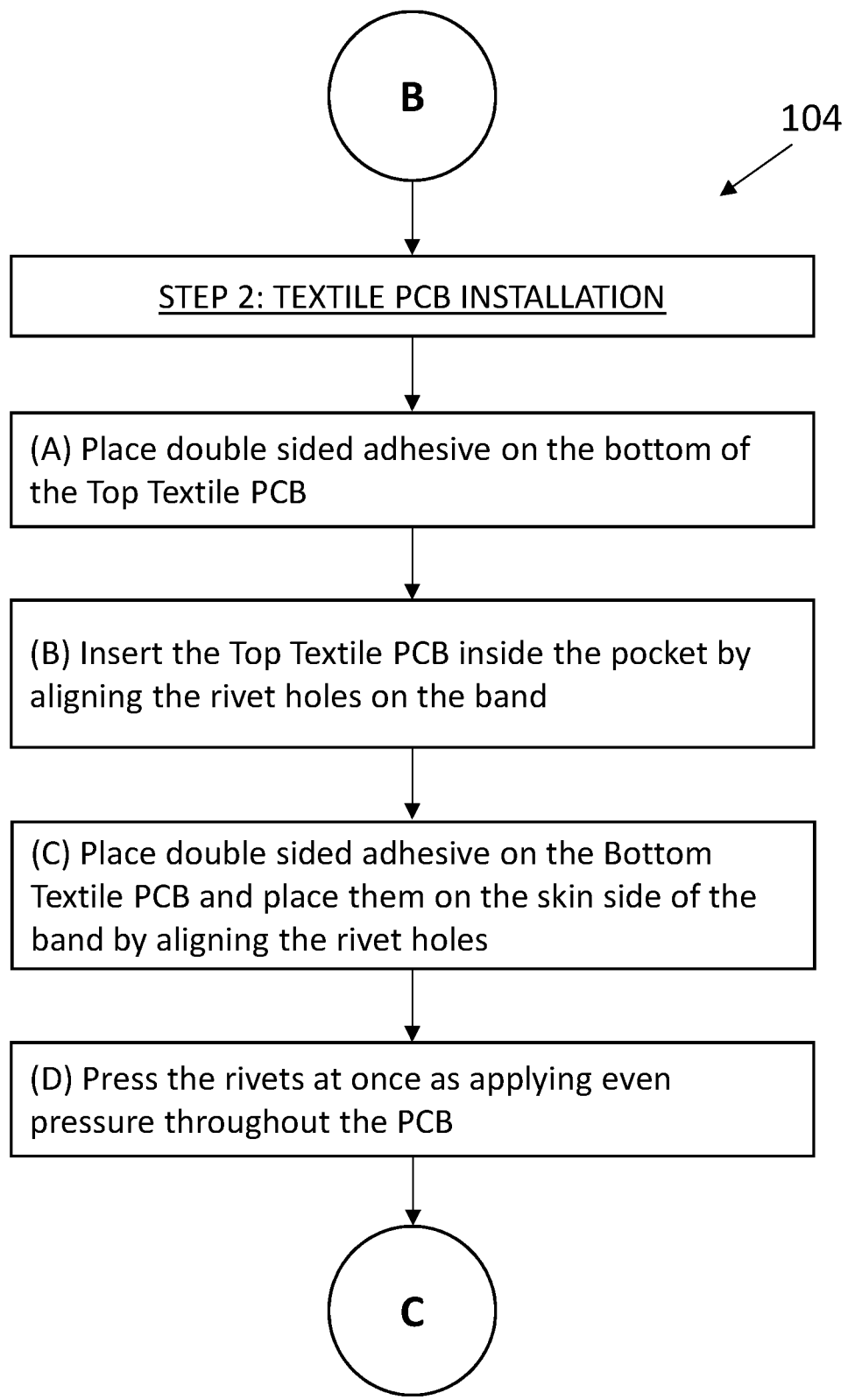
Figure 19:
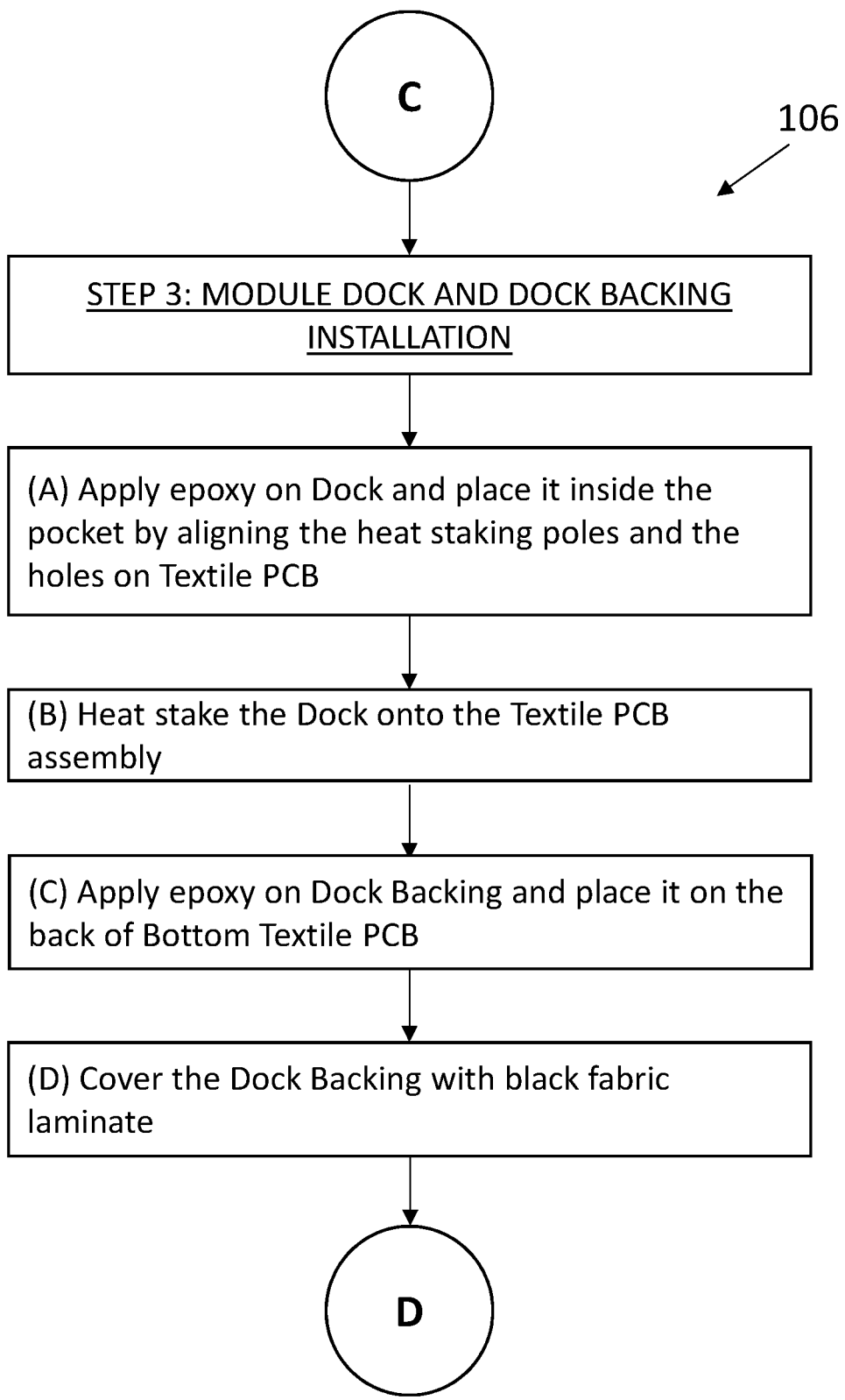
Figure 20:
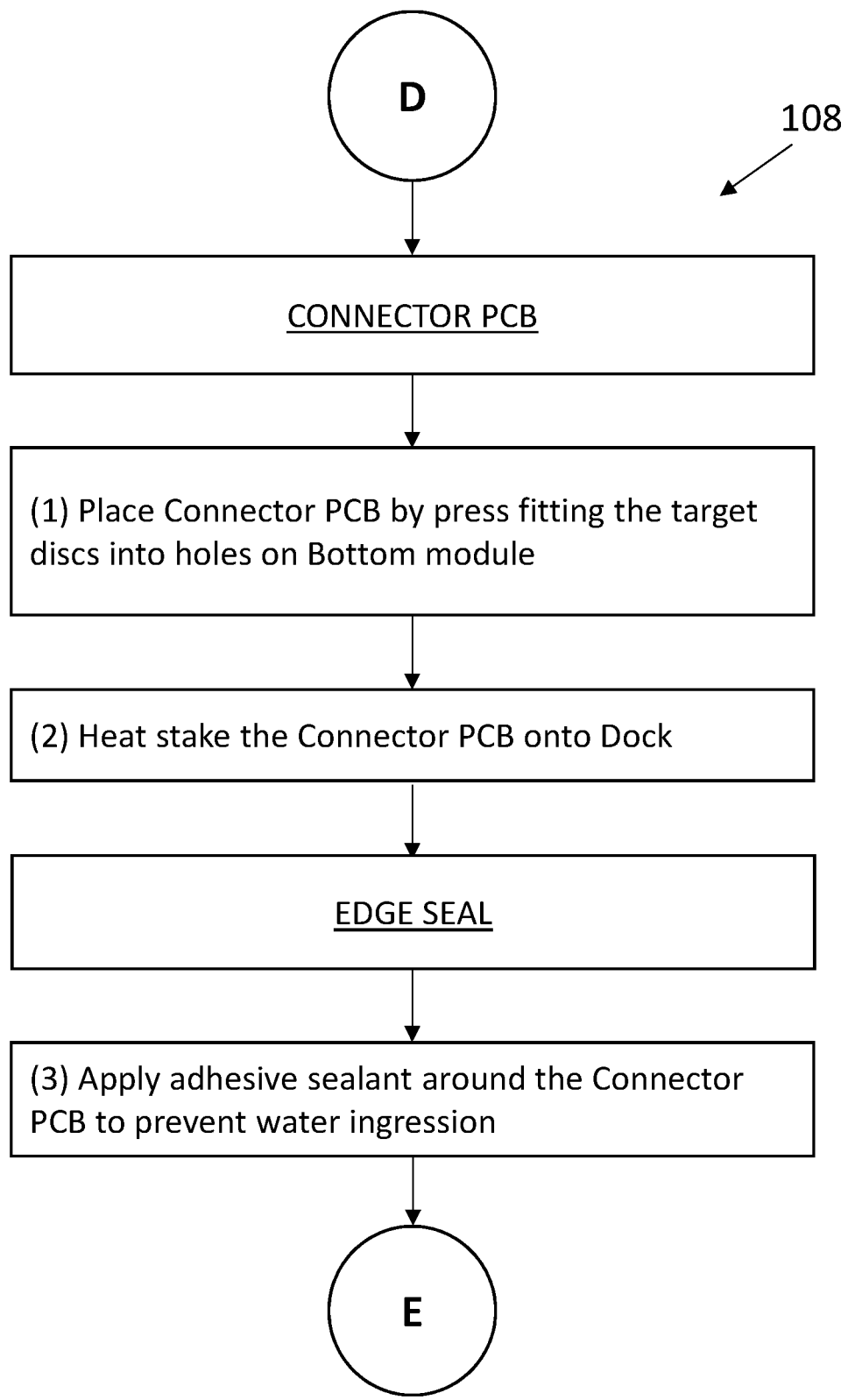
Figure 21:
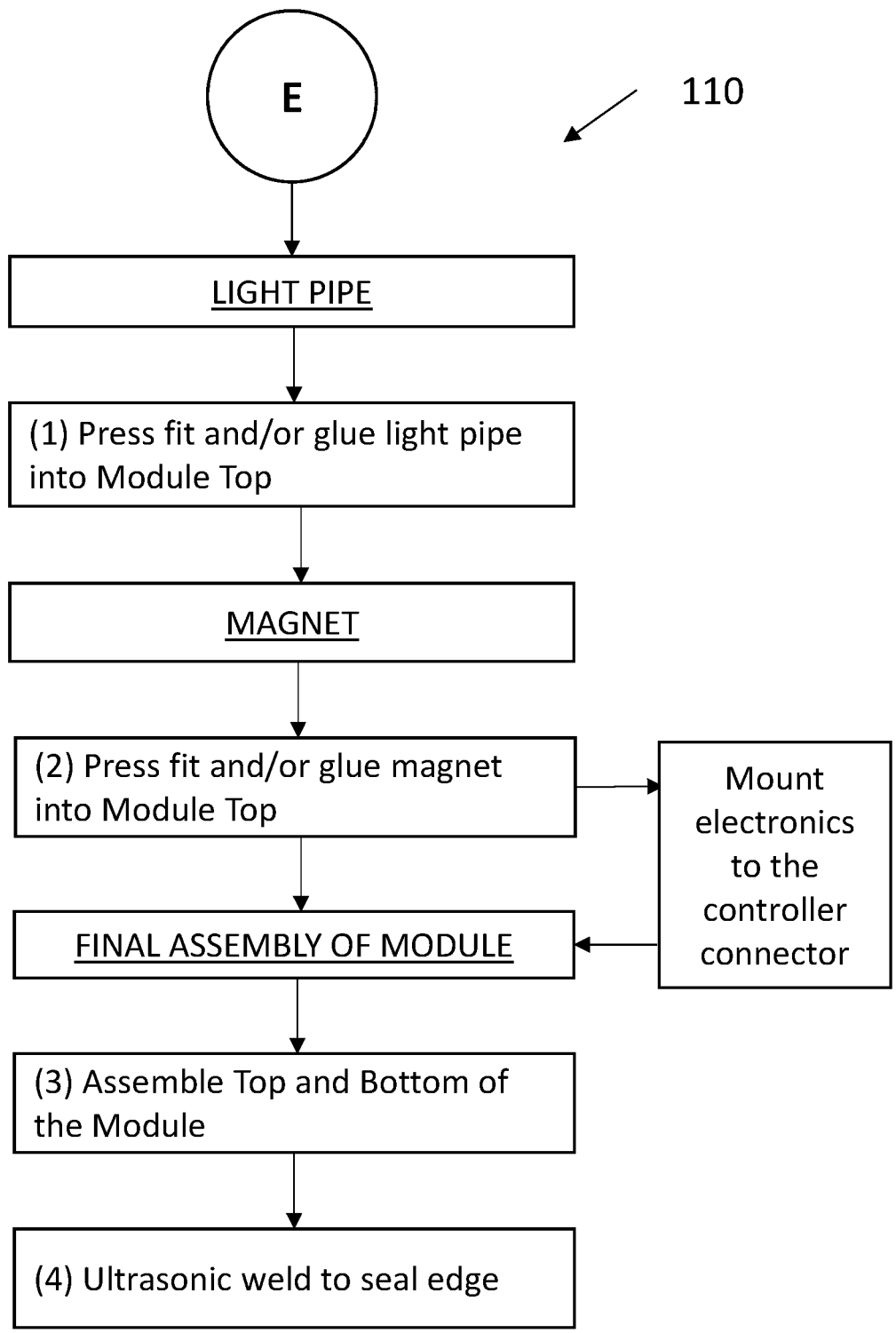

In fabrication of the overall assembly 10, the following example manufacturing processes can be performed. FIG. 17 shows an example process 102 for manufacture of the textile substrate 34 including the conductive pathways 80 (e.g. circuits containing conductive wires/fibres with attached sensors/actuators applied on or otherwise interlaced, knit/woven, with the fibres of the textile substrate 34). FIG. 18 shows an example method steps 104 to manufacture the sandwich of the two substrates 28,30 with the textile substrate 34. Referring to FIG. 19, shown is a method 106 to fasten (e.g. mechanical) the module docking station 14 to the first substrate 28 underlying and adjacent to the module docking station 14. Further, the backing 32 is fastened (e.g. adhesive) to the second substrate 30 underlying and adjacent to the backing 32. FIG. 20 is an example manufacture 108 of the electrical controller connector 26 onto the housing 18, 24 of the controller device 12. FIG. 21 is a method of manufacture 110 for the main controller device 12, including mounting of the components 16, 20, 22 within the interior 86 of the housing 18, 24 and sealing the housing 18, 24.

As shown above by example, the overall assembly 10 included the controller device 12, the module dock station 14 fixedly connected to the substrate(s) 28, 30, and the substrates 28, 30 fixedly connected to the textile substrate 34 (having the plurality of conductive pathways 80). As such, the controller device 12, once assembled, is both mechanically and electrically releasably securable to the module dock station 14, in order to effect electrical communication between the electronics 22 of the controller device 12 and the conductive pathways 80 of the textile substrate 34.

Accordingly, described by example only is: (a) light pipe 16, (b) top enclosure 18, (b) magnet 20, (c) main electronics 22 which can contain (d) the main PCB 28, (e) battery 70 and (f) other electronic components 72, 74, 76, (g) bottom enclosure 24, which holds (h) the connector PCB 26, (i) module dock 14, (j) top textile PCB 28 which are located above the (j) textile band 34 and under the (k) textile pocket 35 and the (l) bottom textile PCB 30 and (m) fabric and laminate padding 32, which are located below the textile band 34.

Further, the embodiments comprise apparatus and methods to make a reliable interconnection between electronic devices 12 and smart textiles 34. The embodiments facilitate the electronic device 12 to maintain a robust electrical connection to electrically conductive circuits 80 on the smart textile 34 while also being securely mechanically fastened to the smart textile 34, thus acquiring the ability to withstand mechanical shock, torsion, stretch and other stresses to which the smart textile 34 or electronic devices 12 may be subject to.

In some embodiments the textile band 34 or textile substrate 34 may contain no electrical or electronic components. In some embodiments, the textile substrate 34 may contain only electrically conductive circuits 80, such as electrically conductive yarn, fiber or printed electronic circuits. In other embodiments, the textile substrate 34 may contain fully functional and active electronic components, sensors, circuits and the like.

For the purposes of a wearable smart textile 34 worn on the body, the direction of below the textile band 34 would be interpreted as being closer to the body and above the textile band 34 would be farther away from the body. The textile pocket 35 is preferably a structure which is raised above the textile band 34 and fabricated by knitting into the textile band 34 knit structure.

In some embodiments, the textile substrate 34 (also called the textile band 34) has successfully incorporated health monitoring sensors in the form of ECG sensor pads, respiratory monitoring sensors and bio-impedance monitoring sensors. These sensors are electrically connected to conductive circuits 80 within the textile band 34, which are then connected using rivets 29, eyelet or grommets 42 leading to the hard electronics 22 (e.g. mounted on the PCB 78). In other embodiments, the main electronics PCB 78 has also successfully incorporated motion sensors and temperature sensors onto the module PCB 78, as part of the electronics 22.

FIG. 17 illustrates embodiment comprising textile form factors to which the textile substrate 34 has been successfully applied, including: underwear, bra and shirts. It can be appreciated that the embodiments are applicable to any form of textile substrate 34 or flexible substrate 34 exhibiting similar properties to a textile or fabric.

FIG. 18 illustrates the steps relating to assembling the top textile PCB 28 onto the textile band 34 with this embodiment comprising steps, including: (1) Placing an adhesive material A on the bottom side of the top textile PCB 28, (2) Inserting the top textile PCB 28 inside the textile pocket 35 by aligning the holes 42 on the top textile PCB 28 to the matching pre-punched rivet holes 34b onto the textile band 34, (3) Placing double-sided adhesive A on the bottom textile PCB 30 and placing it on the opposite side 34a of the textile band 34 to the top textile PCB 28, also aligning to the pre-punched rivet holes 34b in the textile band 34, and (4) Pressing the rivets 29 at the same time as applying even pressure to the PCBs 28, 30.

Steps 1-4, above, create a robust and secure mechanical and electrical connection between the top textile PCB 28, the bottom textile PCB 30 and the textile band 34. In regions where an electrical connection is required, the pre-punched rivet holes 34b in the textile band 34 can be located such that an electrical conductive circuit 80 in the textile band 34 is physically in contact with the metal rivet 29 an/or the conductive locations 42 (e.g. part of the conductive pathways 43 positioned on the underside of the first substrate 28 (and thus able to be placed into direct contact with the surface 34a of the textile substrate 34). It should be noted that rivet 29 can also mean eyelet, grommet or similar type of metal fastening method.

The textile band pocket 35, which is fabricated in such a manner as to be raised above the surface 34a of the textile band 34 facilitating just enough room for the module dock housing 50 to fit snugly within the pocket 35, while also facilitating it to be removed when necessary.

FIG. 19 illustrates the steps 106 relating to assembling the module dock 14 and dock backing 32 into the textile band 34, with this embodiment comprising steps, including: (1) Applying epoxy to the dock 14 and placing it inside the pocket 35 by aligning the heat stacking poles 90 to the holes 28b, 30b on the textile PCBs 28,30, (2) Heat staking the dock 14 onto the textile PCB 28, 30, 34 assembly, (3) Applying epoxy to the dock backing 32 and placing it on the back of the bottom textile PCB 30, and, (4) Covering the dock backing 32 with a fabric, preferably laminated.

FIG. 20 illustrates the steps 108 relating to assembling the connector PCB 26 into the bottom module enclosure 24 with this embodiment comprising the steps of: (1) placing and press-fitting the connector PCB target discs 26 into the bottom module holes 79a, (3) heat staking the connector PCB 26 onto the dock body 14a, (4) applying adhesive sealant around the connector PCB 26 to prevent water ingression between the body 14a and the connector 26.

FIG. 21 illustrates the steps 110 relating to assembling the light pipe 16 and magnet 20 and corresponding electronics 22 into the module top enclosure 18 and assembling the top 18 and bottom 24 module enclosures together with this embodiment comprising the steps of: (1) Press fitting and/or gluing the light pipe 16 into Module Top 18, (2) Press fitting and/or gluing the magnet 20 into Module Top 18 as well as connecting the electronics 22 (e.g. via the PCB 78 together with the connector 26) in order to electrically connect the conductive pathways 76 of the electronics 22 with the connectors of the connector 26), (3) Assembling the Top 18 and Bottom 24 of the Module 12 together, and (4) Ultrasonically welding to seal the edges of the top 18 and bottom 24 module.

Other options for manufacture can include generally processes such as but not limited to:
1) the process of assembly comprises the steps of: assembling the top textile PCB onto the textile band; placing an adhesive material on the bottom size of the top textile PCB; inserting the top textile PCB inside the textile pocket by aligning the holes on the top textile PCB to the matching pre-punched rivet holes onto the textile band; placing double-sided adhesive on the bottom textile PCB and placing it on the opposite side of the textile band to the top textile PCB, also aligning to the pre-punched rivet holes in the textile band; and pressing the rivets at the same time as applying even pressure to the PCBs;

2) in regions where an electrical connection is needed, the pre-punched rivet holes in the textile band can be located such that an electrical conductive circuit in the textile band is physically in contact with the metal rivet;

3) the textile band pocket can be fabricated in such a manner as to be raised above the surface of the textile band providing just enough room for the module dock housing to fit snugly within the pocket, while also allowing it to be removed when used;

4) assembling the module dock and dock backing into the textile band; applying epoxy to the dock and placing it inside the pocket by aligning the heat stacking poles to the holes on the textile PCBs; heat staking the dock onto the textile PCB assembly; applying epoxy to the dock backing and placing it on the back of the bottom textile PCB; and covering the dock backing with a fabric, preferably laminated;

5) assembling the connector PCB into the bottom module enclosure; placing and press-fitting the connector PCB target discs into the bottom module holes; heat staking the connector PCB onto the dock; and applying adhesive sealant around the connector PCB to prevent water ingression; and/or 6) assembling the light pipe and magnet into the module top enclosure and assembling the top and bottom module enclosures together; press fitting and/or gluing the light pipe into Module Top; press fitting and/or gluing the magnet into Module Top; assembling the Top and Bottom of the Module together; and ultrasonically welding to seal the edges of the top and bottom module.

Thus, it is appreciated that the optimum dimensional relationships for the parts of the invention, to include variation in size, materials, shape, form, function, and manner of operation, assembly and use, are deemed readily apparent and obvious to one of ordinary skill in the art, and all equivalent relationships to those illustrated in the drawings and described in the above description are intended to be encompassed by the present invention.

Furthermore, other areas of art may benefit from this method and adjustments to the design are anticipated. Thus, the scope of the invention should be determined by the appended claims and their legal equivalents, rather than by the examples given.

The embodiments of the invention in which an exclusive property or privilege is claimed are defined as follows:

1. A docking station assembly for providing a releasably secure connection between an electronic controller device and one or more conductive pathways of a textile substrate comprising:

a module dock station having a body fixedly connected to a substrate assembly mounted on the textile substrate, the body exposing an electrical dock connector configured for mating with an electrical controller connector of the electronic controller device;

the substrate assembly comprising:

a first substrate positioned to one side of the textile substrate within a textile pocket that includes one or more first electrical connection locations, such that the one or more first electrical connection locations of the first substrate are aligned with the one or more conductive pathways, the first substrate having the electrical dock connector mounted thereon and electrically connected to the one or more first electrical connection locations by one or more respective substrate conductive pathways;

a second substrate positioned on the other side of the textile substrate opposite the one side, the second substrate having one or more second electrical connection locations aligned with the one or more first electrical connection locations; and one or more respective fasteners fastening the one or more second electrical connection locations with the one or more first electrical connection locations, thus fixedly securing the textile substrate between the first substrate and the second substrate;

wherein the one or more first electrical connection locations are in electrical contact with the adjacent one or more conductive pathways, wherein the textile pocket is sized for the module dock station to fit snugly therein, wherein the textile substrate comprises at least one of an active electronic component, a sensor, or a circuit, and wherein the one or more respective fasteners are electrically conductive and in physical contact with the one or more conductive pathways.

2. The docking station assembly of claim 1, wherein the textile pocket is preferably a structure which is raised above an adjacent surface of the textile substrate and fabricated by knitting into a knit structure of the textile substrate.

3. The docking station assembly of claim 1, wherein the one or more respective fasteners are rivets.

4. The docking station assembly of claim 1, wherein the one or more first electrical connection locations are eyelets or grommets leading to the electrical controller connector via the one or more respective substrate conductive pathways.

5. The docking station assembly of claim 4, wherein the one or more respective substrate conductive pathways are traces of PCB circuitry, such that the first substrate is a PCB.

6. The docking station assembly of claim 1, wherein the textile substrate is incorporated into a garment selected from the group consisting of: a band; underwear; a bra; and a shirt.

7. The docking station assembly of claim 1 further comprising a releasable mechanical connector located on the body, the releasable mechanical connector facilitating a releasably secure mechanical connection between the controller device and the body.

8. The device of claim 1, wherein the electrical dock connector mates with the electrical controller connector via a pin and socket configuration.

* * * * *